(12) United States Patent
Keenan et al.

(10) Patent No.: US 8,257,338 B2
(45) Date of Patent: Sep. 4, 2012

(54) MEDICAL MICROBUBBLE GENERATION

(75) Inventors: James A. Keenan, Ottawa (CA); Adrian Blenkinsop, Ottawa (CA); Phillipe Genereux, Ottawa (CA)

(73) Assignee: Artenga, Inc., Ottawa (CA)

( * ) Notice: Subject to any disclaimer, the term of this patent is extended or adjusted under 35 U.S.C. 154(b) by 478 days.

(21) Appl. No.: 12/115,299

(22) Filed: May 5, 2008

(65) Prior Publication Data

US 2008/0269668 A1  Oct. 30, 2008

Related U.S. Application Data

(63) Continuation-in-part of application No. 11/588,995, filed on Oct. 27, 2006, now abandoned.

(51) Int. Cl.
*A61M 31/00* (2006.01)
(52) U.S. Cl. ........................ 604/500; 424/9.52
(58) Field of Classification Search ............... 604/24, 604/82, 83, 84, 85, 87, 500, 903; 424/9.5, 424/9.51, 9.52, 450; 128/897, 898
See application file for complete search history.

(56) References Cited

U.S. PATENT DOCUMENTS

| | | | |
|---|---|---|---|
| 5,215,680 A | 6/1993 | D'Arrigo |
| 5,352,436 A | 10/1994 | Wheatley |
| 5,425,580 A | 6/1995 | Beller |
| 5,540,909 A | 7/1996 | Schutt |
| 5,556,610 A | 9/1996 | Yan |
| 5,578,292 A | 11/1996 | Schneider |
| 5,585,112 A | 12/1996 | Unger et al. |
| 5,605,673 A | 2/1997 | Schutt |
| 5,626,833 A | 5/1997 | Schutt |
| 5,639,443 A | 6/1997 | Schutt |
| 5,656,211 A | 8/1997 | Unger et al. |
| 5,695,741 A | 12/1997 | Schutt |
| 5,707,606 A | 1/1998 | Quay |
| 5,715,824 A | 2/1998 | Unger et al. |
| 5,720,938 A | 2/1998 | Schutt |
| 5,733,527 A | 3/1998 | Schutt |
| 5,773,024 A | 6/1998 | Unger et al. |

(Continued)

FOREIGN PATENT DOCUMENTS

CA  2456988  2/2003

(Continued)

OTHER PUBLICATIONS

English Translation of WO 2008018484 A1 as provided by the European Patent Office's Espacenet.*

(Continued)

*Primary Examiner* — Kevin C Sirmons
*Assistant Examiner* — Kami A Bosworth
(74) *Attorney, Agent, or Firm* — Albert Peter Durigon

(57) ABSTRACT

Medical apparatus and processes controllably generate medically useful micro or nano bubbles of medically desirable and controllably selectable size, size distribution, homogeneity and concentration (and/or other key bubble parameters) for patient infusion, and/or which may incorporate therapeutic or other agents for patient infusion and/or may be combined with therapeutic or other agents prior to infusion into patients. The bubble generation apparatus and processes controllably permit the adjustment and selection of key bubble parameters through bubble generation actuation and orientation techniques and through selection of bubble fluid compositions in order to facilitate medical research and/or to optimize treatment for imaging, therapy, sonoporation, inertial and non-inertial cavitation, and acoustic activation, among other medical uses. Disposable cartridges containing such bubbles are provided and may include means for patient infusion.

16 Claims, 7 Drawing Sheets

U.S. PATENT DOCUMENTS

| | | | |
|---|---|---|---|
| 5,798,091 A | 8/1998 | Trevino | |
| 5,853,752 A | 12/1998 | Unger et al. | |
| 5,935,553 A | 8/1999 | Unger et al. | |
| 6,019,960 A | 2/2000 | Schutt | |
| 6,036,644 A | 3/2000 | Schutt | |
| 6,039,557 A | 3/2000 | Unger et al. | |
| 6,056,943 A | 5/2000 | Schutt | |
| 6,146,657 A | 11/2000 | Unger et al. | |
| 6,245,318 B1 | 6/2001 | Klibanov | |
| 6,245,319 B1 | 6/2001 | Quay | |
| 6,258,339 B1 | 7/2001 | Schutt | |
| 6,258,378 B1 | 7/2001 | Schneider | |
| 6,280,704 B1 | 8/2001 | Schutt | |
| 6,280,705 B1 | 8/2001 | Trevino | |
| 6,287,539 B1 | 9/2001 | Schutt | |
| 6,372,195 B1 | 4/2002 | Schutt | |
| 6,416,740 B1 | 7/2002 | Unger | |
| 6,572,840 B1 | 6/2003 | Toler | |
| 6,638,244 B1 * | 10/2003 | Reynolds | 604/82 |
| 6,706,253 B2 | 3/2004 | Schutt | |
| 6,896,659 B2 | 5/2005 | Conston | |
| 6,953,569 B2 | 10/2005 | Schutt | |
| 7,060,049 B2 * | 6/2006 | Trombley et al. | 604/82 |
| 7,998,106 B2 * | 8/2011 | Thorne et al. | 604/32 |
| 2002/0051750 A1 | 5/2002 | Schutt | |
| 2002/0098151 A1 | 7/2002 | Schutt | |
| 2002/0123719 A1 * | 9/2002 | Lavi et al. | 604/82 |
| 2003/0125727 A1 | 7/2003 | Truckai | |
| 2003/0191446 A1 | 10/2003 | Tachibana | |
| 2004/0025876 A1 | 2/2004 | Miller | |
| 2004/0249341 A1 * | 12/2004 | Newbrough et al. | 604/87 |
| 2004/0253183 A1 | 12/2004 | Uber | |
| 2007/0183976 A1 | 8/2007 | Unger | |
| 2008/0014627 A1 | 1/2008 | Merchant | |
| 2008/0019904 A1 | 1/2008 | Boehmer | |
| 2010/0087779 A1 * | 4/2010 | Shimizu et al. | 604/82 |

FOREIGN PATENT DOCUMENTS

| | | |
|---|---|---|
| CA | 2577457 | 4/2008 |
| DE | 29522119 | 12/1999 |
| EP | 0711179 | 2/1995 |
| EP | 1228770 | 8/2002 |
| EP | 1550464 | 7/2005 |
| RU | 2131744 | 6/1999 |
| WO | WO9516467 | 6/1995 |
| WO | WO0247744 | 6/2002 |
| WO | WO2004082749 | 9/2004 |
| WO | WO2005/105181 | 11/2005 |
| WO | WO2006046202 A1 | 5/2006 |
| WO | WO2006127953 | 11/2006 |
| WO | WO2007002933 A2 | 9/2007 |
| WO | WO 2008/018484 A1 * | 2/2008 |

OTHER PUBLICATIONS

English Translation of WO 2008018484 A1 as provided by the Japanese Patent Office's AIPN.*

Mattrey, The potential role of perfluorochemicals (PFCS) in diagnostic imaging, Art. cells, blood sub., and immob. biotech., 22 (2), 295-313 (1994).

Price, Delivery of colloidal particles and red blood cells to tissue through microvessel ruptures created by targeted microbubble destruction with ultrasound, Circulation, Sep. 29, 1998; 98 (13): 1264-7).

Thomas, Towards a targeted surfactant stabilized ultrasound contrast agent, dissertation, Drexel University, Jan. 2002.

Oeffinger, Development and characterization of a nano-scale contrast agent, Ultrasonics 42 (2004) 343-347.

Wheatley, Structural studies on stabilized microbubbles: development of a novel contrast agent for diagnostic ultrasound, Reactive Polymers 25 (1995) 157-166.

* cited by examiner

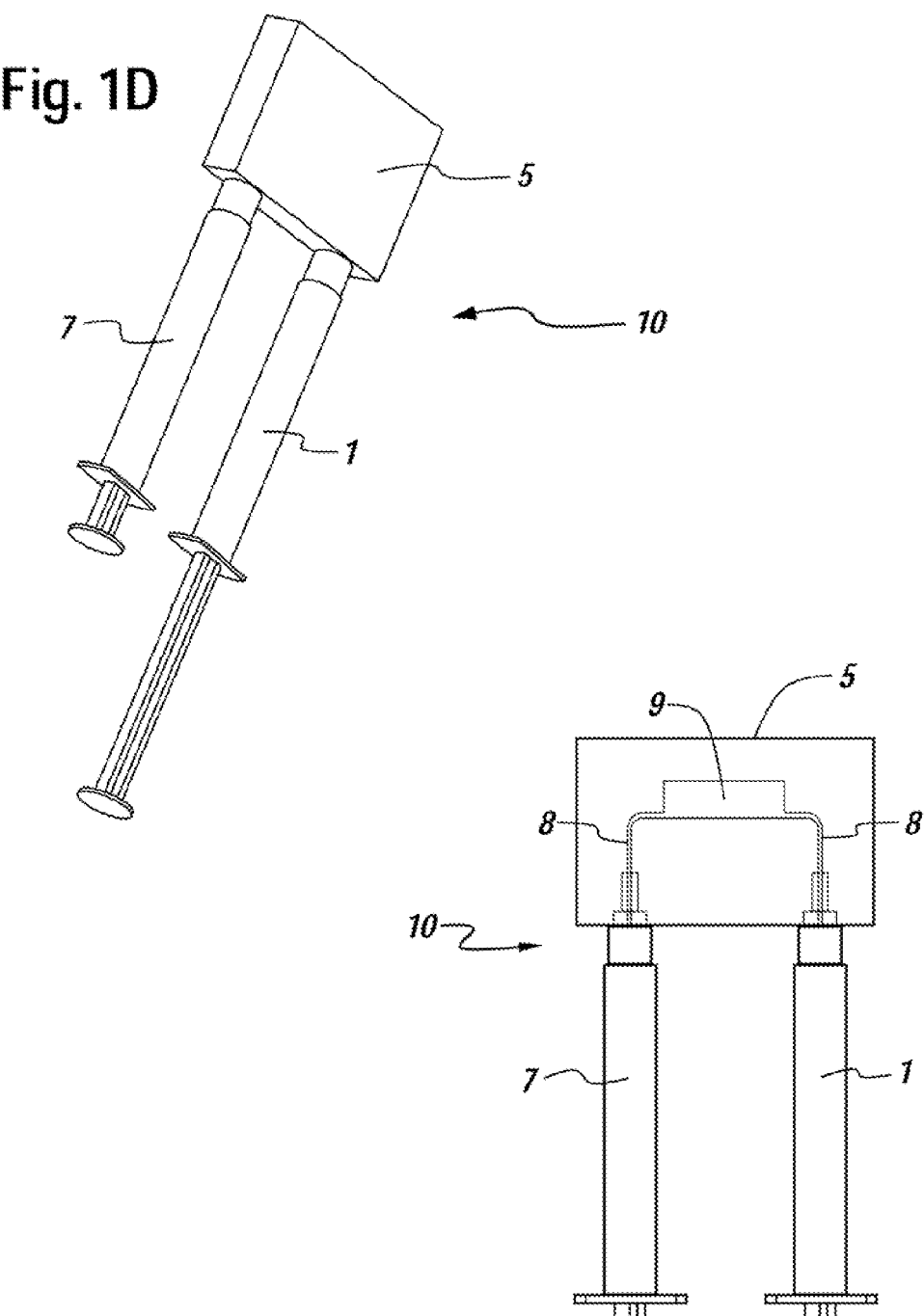

MEDICAL MICROBUBBLE GENERATION

CROSS-REFERENCE TO RELATED APPLICATIONS

This invention is a continuation-in-part of, commonly-assigned US utility patent application entitled Microbubble Medical Devices, Ser. No. 11/588,995, filed Oct. 27, 2006, now abandoned, of James Keenan, incorporated herein by reference.

FIELD OF THE INVENTION

This invention is drawn to the field of medical microbubble generation, and more particularly, to medical microbubble generating apparatus and processes generating medically useful bubbles with medically desirable properties, and to disposables containing infusates of such bubbles that are produced by the microbubble generating processes.

BACKGROUND TO THE INVENTION

Gas-filled microbubbles are a proven contrast agent, a means to enhance ultrasound imaging for medical diagnosis and in particular echocardiograms. They are infused into the bloodstream and, as they pass beneath the transducer, the ultrasound image is brightened and vascular details are revealed due to their echogenic properties. Microbubbles may also be used for therapeutic applications. This includes disruption of bubbles with ultrasound in order to permeabilize tissue and therefore enhance drug uptake and efficacy. This technique has been referred to as acoustic activation, sonoporation, contrast-mediated drug delivery, inertial cavitation and non-inertial cavitation.

A variety of acoustically activated drug delivery systems exist including gas bubbles combined with drugs, drugs encapsulated in microspheres, biodegradable polymer and drug solution gas bubbles, drug impregnated microsponges, injectable nanoparticles such as vesicles, micelles, and liposomes, and other drug carrying particles, bubbles, or spheres that permit acoustic activation of therapeutic agents.

Acoustically activated drug delivery systems are typically administered to a patient and then activated by extracorporeal ultrasound to increase the permeability of cell membranes to allow drugs to better penetrate cells, enhance drug uptake, and hence improve the treatment efficacy.

Acoustic activation may permit localized drug delivery. The physician may apply ultrasound once the drug and cavitation nuclei, typically microbubbles, are delivered to a point of interest within a patient, in order to release the drug at the disease site. Localized drug delivery permits a high dosage of toxic drugs to improve treatment effectiveness and may minimize negative side effects to healthy tissue. Permeabilization of tissue in order to increase drug uptake may or may not be done in combination with localized delivery.

Focused acoustic activation may permit localized drug delivery. The therapeutic agent and microbubbles may be administered systemically within a patient and special Focused ultrasound used to locally sonicate an area of interest, such as a tumour, in order to permeabilize tissue within the disease site. The therapeutic agent may be administered to the brain through the carotid artery and special trans-skull Focused ultrasound used to locally sonicate an area of interest in order to overcome the blood brain barrier and permit effective drug treatment.

Ultrasound energy may cause gas microbubbles to resonate or burst into smaller fragments, and may induce bubble resonance that physically deforms cell membranes, or cavitation, or microstreaming, or the perforation of cell membranes. Bubble resonance is typically described as sonoporation or non-inertial cavitation, while the bubble destruction is described as inertial cavitation.

The therapeutic agents may be chemotherapy drugs, gene therapy, fusion proteins, and other agents.

Direct injection of chemotherapy drugs into tumours is typically not done, as this does not improve patient outcome. Cancers may develop resistance to drugs and render chemotherapy useless. Acoustic activation researchers have destroyed human, drug-resistant tumours in rodents using cavitation nuclei and ultrasound.

Acoustic activation technology shows promise for the treatment of drug resistant cancer tumours, vascular disease, neurological diseases, and other diseases. Efficacy may be enhanced by infusing drugs with bubbles and enhancing cell permeability with ultrasound energy. Further benefits may be obtained by infusing transient gas microbubbles in combination with acoustically activated drug delivery release systems to enhance the local cavitation effects.

Presently, acoustically activated drug delivery systems are typically hard-shelled, persistent, gas microbubbles formulated in a pharmaceutical setting. They are designed to persist through to administration to a patient. Such products are required to maintain integrity through the shock, vibration, and temperature changes of transportation and to persist over time through to administration. Such formulations may include complex design and processing features, for example, are typically lipid, polymer, or polymer and solvent based. However, these persistent systems must also dissipate or degrade in the patient once administered and activated. These polymers and any other components are required to biodegrade with minimal negative side effects.

Acoustically activated drug delivery systems may range in size from nano scale, sub micron, up to 1000 microns, with a one to ten micron size typical. Size preference depends upon the resonant frequency, or a harmonic, of the bubble or particle to be activated at a particular ultrasound frequency, and may also depend upon the desired release rates of the encapsulated drugs. Increased size uniformity would encourage effective and more complete activation.

Acoustic activation techniques include inertial cavitation, where gas microbubbles are destroyed by ultrasound energy and bubble shell fragments perforate cells to create nano sized openings, and non-inertial cavitation or sonoporation, where ultrasound energy causes bubbles to resonate. Researchers have demonstrated in vivo therapeutic enhancement with both techniques. In addition, sonophoresis involves the application of ultrasound, or ultrasound and cavitation nuclei such as microbubbles, to increase the permeability of surface cells, such as the skin or cornea, in order to improve the delivery of topically applied drugs.

In the field of oncology, chemotherapy is typically administered intravenously for systemic treatment. Some localized drug delivery techniques are practised, for example, targeted drugs, shunting techniques to direct a drug through a tumour vasculature, direct ethanol or acid injection for ablation of liver tumours, and interoperative peritoneal techniques including hyperthermic intraoperative peritoneal chemotherapy (HIPEC) where chemotherapy is heated and poured directly into the abdomen during open surgery in order to treat tumours too small to be visually detected.

In terminal cases, drug treatment may be ineffective as the metastasis of the disease causes it to reappear after initial chemotherapy cycles and the debilitating side effects of systemic chemotherapy preclude repeat systemic chemotherapy administration at effective dose levels. As well, a cancer may have inherent or developed drug resistance.

Promising new medicines, in particular gene therapy drugs, may be unsuitable for clinical use due to inadequate delivery techniques and other new drugs may possess unduly high toxicity.

Therefore the following needs exist in oncology: a means to enhance locally improved uptake of chemotherapy in a tumour in order to achieve effective treatment with less dose and toxicity, a means to overcome drug resistance, and a means to effectively deliver new medicines.

Oncologists do not currently have a means to provide patients with a flexible, acoustically activated therapy, i.e. the means to enhance a variety of drugs, or combination of drugs, with improved drug uptake and efficacy and reduced side effects.

High intensity Focused ultrasound (HIFU) is a means to induce cell necrosis in diseased tissue, for example to destroy tumours through heat ablation. Heat ablation probes typically require about fifteen minutes in which to heat up to effective ablation temperatures and a similar cool down period. This duration may preclude treatment if patients are in overall poor health and require a number of tumours to be destroyed, add to the cost and invasiveness of the technique, including anaesthesia requirements. A means to reduce treatment duration is desirable.

In a serious pandemic, effective vaccines may be developed but until sufficient quantities are available medical authorities may be unable to treat all effected patients. A means to maximize the number of patients treated with a limited supply of vaccine would be highly desirable. This could be accomplished through enhanced delivery techniques, for example direct vaccine delivery to the spleen combined with microbubbles and acoustic activation in order use less vaccine dose per patient.

Accordingly, there is a need for medical bubble generating apparatus and processes controllably providing medical bubbles (micro and nano) useful for therapy, sonoporation, inertial and non-inertial cavitation, acoustic activation, targeted delivery and ultrasound imaging, among other medical uses, that have medically desirable and selectable sizes, size distributions, concentrations and homogeneities, among other key bubble parameters.

SUMMARY OF THE INVENTION

Medical bubble generating apparatus and processes are disclosed providing medical bubbles useful for therapy, sonoporation, inertial and non-inertial cavitation, acoustic activation, targeted delivery and ultrasound imaging among other medical uses, that have medically desirable and selectable sizes, size distributions, concentrations and homogeneities, among other key bubble parameters.

Novel bubble generating means are disclosed: a capillary tube and mix chamber system with various reciprocating, orientation, and actuation features including a purge cycle and a centrifuge cycle in order to control and adjust key bubble parameters. These parameters include mean bubble size, size distribution, concentration (bubbles/unit volume), and concentration homogeneity throughout the carrier liquid, and optimizing of such parameters will result in more effective acoustic activation.

The medical device comprises a fluid vessel for holding a fluid or fluids, a fluid delivery means operatively connected to the fluid vessel for applying a pressure and causing the fluid or fluids to travel a flow path, and a bubble generating means for generating bubbles comprised of the fluid or fluids. The fluid or fluids passing through the bubble generating means, which may be comprised of a carrier liquid and a gas head space, is termed herein as "bubble fluid". The bubbles generated are micro or nano sized and typically include shell and globule components.

The bubble fluid may include a suitable gas for in vivo use, such as, but not limited to, perfluorocarbons (pfc), sulfur hexafluoride, air, osmotic agents such as nitrogen, or combinations of different gas types. The bubble fluid may include a suitable bubble shell material for in vivo use, such as, but not limited to, surfactants, lipids, polymers, proteins, or combinations of materials.

The fluid delivery means causes fluid in the vessel to travel a flow path, usually along a conduit or vessel such as a syringe. The fluid delivery means may be a plunger on a standard medical syringe, a syringe pump, variable speed fluid transfer pump, peristaltic pump, or other means to pump fluids, and also contemplates pressurization in combination with regulators, for example, compressed gas with a gas regulator.

The fluid delivery means may be manually actuated, driven by mechanical means such as compression or extension springs, or other mechanical methods, by electromechanical means such as an electric motor, solenoid drive, programmable syringe pump, or other electromechanical means, or by pneumatic or hydraulic means. Where the fluid is a compressed gas, the fluid delivery means may include compressed gas force and suitable regulators. A variety of means are contemplated and may be selected depending on a variety of factors such as the manner of operation of the bubble generating means, the size of the bubbles, the relative viscosity of the bubble fluid and carrier fluid, and other factors, as will be appreciated.

The bubble fluid or fluids may be caused to travel a flow path into an additional fluid vessel or vessels. A fluid delivery means operatively connected to the fluid vessel or vessels for applying a pressure may cause the fluid or fluids to be reciprocated back along the flow path and bubble generating means to the first fluid vessel and this reciprocating fluid flow may be repeated for a plurality of cycles and/or at different flow rates so as to provide medically useful microbubbles of medically desirable side, size distribution, concentration and homogeneity depending on the composition selected for the bubble and/or other fluids and/or on the medical application. A predetermined number of reciprocal cycles (1 or more) and reciprocal half cycles (even, odd, or zero) determined to controllably provide preselected, medically desirable bubble properties for different medical applications may be employed.

The fluid vessel or vessels, flow path, and bubble generating means may be reoriented, either manually or through electromechanical, pneumatic, hydraulic, or other actuation means, during bubble generation or during a purge cycle in order to optimize the bubble parameters. In one presently preferred embodiment, the fluid or fluids are caused to travel a flow path oriented in a vertical direction with the bubble fluid driven from top to bottom in order to utilize bubble buoyancy to ensure a consistent bubble concentration distribution throughout the carrier fluid. In one presently preferred embodiment, the fluid vessel or vessels and bubble generating means are arranged in-line in a disposable, removable cartridge which is vertically oriented and inverted every half reciprocal cycle in order to utilize bubble buoyancy and in another presently preferred embodiment, the fluid vessel or vessels and bubble generating means are arranged in a disposable, removable cartridge having a U-shaped cartridge, where the bubble generating means is provided along the base of the U-shape and each of the one or more fluid vessel or vessels is vertically oriented along another one of the legs of the U-shaped disposable, removable cartridge.

The bubble fluid may be combined within a second or multiplicity of fluids. Additional fluids may be contained within a second vessel or within a conduit into which both the bubble fluid and the additional fluid flows.

A disposable, removable cartridge containing microbubbles (or nano bubbles) generated in accord with the present invention may be used with injection means for delivering the bubble fluid into a body at a desired location, for example, into a tissue mass, tumour, vascular network, muscle, skin, organ, or other suitable structure, depending on the application.

Ultrasound may then be used to image the bubbles in vivo and to disrupt, rupture, resonate, or otherwise activate the bubbles (acoustic activation) at a point of interest.

The injection means includes a hollow needle, catheter, tube, or other surgical instrument that can be inserted within a body to a point of interest, for example, into a tissue mass, tumour, muscle, skin, organ, vein, artery, or other suitable structure, depending on the application, and is structured to permit fluid flow. The injection means could include pouring of the bubble fluid directly from a fluid vessel into the body during open surgery. The term "injection means" is to be broadly understood as including various means for introducing a fluid into a body, including by active injection or passive permeation, or otherwise by infusion.

The bubble fluid may be a liquid or gas, including in the form of a solution, a suspension, a vapour, other fine particulate solids dissolved in a liquid vehicle, a combination, or the like, provided that it is flowable. This fluid may be added to a second fluid which may also be in the form of a solution, a suspension, a vapour, other fine particulate solids dissolved in a liquid vehicle, a combination, or the like, provided that it is flowable. Thus, the device may be used to generate gas bubbles within a liquid carrier, liquid bubbles/droplets within a liquid carrier, liquid bubbles/droplets within a gas carrier, or gas bubbles within a gas carrier. The device may be used with liquefied gas.

The fluid vessel is any vessel that can hold and dispense fluid. For example, the vessel may be in the form of a syringe and the fluid delivery means may be in the form of a plunger for the syringe or a pump. As another example, the fluid vessel may be in the form of a compressed gas vessel and the fluid delivery means in the form of a compressed gas force and suitable regulators. The term "container" may be understood as interchangeable with the term "vessel".

The fluid vessel may contain a therapeutic fluid or a carrier fluid. A therapeutic fluid may be a therapeutic liquid, such as a liquid drug or drug in solution, or contain a therapeutic agent suspended, dissolved, carried, or otherwise conveyed in a suitable liquid vehicle including drug eluting microspheres suspended in a fluid and radiolabelled isotopes. A therapeutic agent may include a variety of drug compounds, or other medicinal or non-medicinal substances, minerals, vitamins, biotherapeutics, vaccines, organic or inorganic substances, imaging-enhancement substances, radioactive substances, and the like, that can be carried in the liquid or gaseous fluid.

The carrier or bubble fluids may include additives chemically compatible with specific therapeutic agents, for example an alcohol-compatible surfactant. This may permit acoustic activation of treatments such as direct ethanol or acid injection in tumours, or injection of liquid radioisotopes or radioactive particles in suspensions.

The bubble fluids may include charged compounds, for example cationic surfactants, in order to enhance drug binding to or drug encapsulation within bubbles or to improve drug effectiveness, for example to enhance transfection of gene therapies.

The medical microbubble generating apparatus of the present invention may be configured as a table-top or floor-supported unit, locally mounted, supported on patient body parts, or configured in other means suitable to a clinical setting. The apparatus may be connected to building utilities, for example to a hospital oxygen gas supply line.

The medical microbubble generating apparatus of the present invention may be comprised of a bubble generating means, for example a sterile, single-use removable, disposable cartridge, and a repeat-use base station, for example to provide fluid delivery, adjust orientation, and incorporate sensors and controls to ensure appropriate bubble generation. The removable, disposable cartridge preferably includes a fluid vessel or vessels, a bubble fluid or fluids, and a bubble generation means or module, for example a capillary tube or tubes and mix chamber or chambers. The medical microbubble generating apparatus in one presently preferred embodiment includes means to deliver fluid, to adjust the fluid delivery actuation, and to orient the fluid or fluids in the consumable on demand in order to optimize or adjust bubble parameters.

In one presently preferred embodiment wherein the fluid vessel and bubble generation means are arranged in-line along a flow path, the medical microbubble generating apparatus positions the removable, disposable cartridge or consumable in multiple orientations in order to use buoyancy and gravity to adjust bubble parameters.

Sensors in the medical microbubble generating apparatus may be used to detect leaks, plugs, or other undesirable defects in the bubble generation means, for example pressure sensor or motor current load monitors could be used to detect blockages or leaks in the bubble generation means and to alert the operator through a graphic user interface or alternate alarm system.

The bubble fluid may be biologically filtered using conventional one-tenth (0.1) or two-tenths (0.2) micron filters. The generating means may be terminally sterilized using a variety of conventional sterilization means, for example gamma sterilization for which gamma radiation compatible materials, for example polycarbonates, are selected.

The medical microbubble generating apparatus may include means to control the fluid temperature, such as refrigeration or heating sources, temperature sensors and controls, thermal insulating materials, and the like, to enhance the bubble generation. Temperature control means in combination with fluid pressure control, may enable a suitable fluid in liquid form to be transformed into micro or nano bubbles and infused into the patient, after which body temperature and pressure may cause the bubbles to change to a gas form for acoustic activation. Bubbles generated by the medical microbubble generating apparatus or device may be heated to body temperature prior to infusion within the patient in order to ensure that the bubble size remains constant from generation to therapeutic use.

The therapeutic agent may be delivered to the point of interest prior to, simultaneously with, or after the delivery of the bubbles in a carrier fluid. The device may include fluid reservoirs for the therapeutic agent or agents, bubble fluid or fluids, and carrier fluid or fluids.

Devices of the present invention includes means for providing nano or micro bubbles through patient infusion means such as a needle or catheter, to enhance the therapeutic efficacy of a drug.

Using apparatus, processes, and removable, disposable cartridges of the present invention, bubbles may be generated proximal to the procedure site, for example, within a hospital pharmacy or operating room, including prior to or during a drug administration procedure, and acoustically activated without substantial delay. This may result in a less complex system and reduce the additives needed to stabilize bubbles generated in pharmaceutical settings, and produce more uniform bubbles. These and other advantages will become apparent to the skilled person.

Using apparatus, processes, and removable, disposable cartridges of the present invention, bubble parameters, for example concentration, composition, size, size distribution, homogeneity, and other bubble parameters may be varied on demand, including immediately prior to or during a drug administration procedure or in vivo.

The bubble generating apparatus and processes of the present invention may employ multiple, repeated fluid delivery cycles through a bubble generation means in order to adjust bubble parameters such as concentration and homogeneity and to improve mixing of the components. Multiple fluid delivery cycles may permit simplification and cost reduction of the bubble generation means, for example the microfluidic geometry of capillary tubes, expansion chambers, and the like. In one presently preferred embodiment, the bubble generation module of the removable, disposable cartridge includes spatially separated single capillary tube and single mix chamber of comparatively smaller and comparatively larger cross-section.

The bubble generating apparatus and processes of the present invention may employ actuation means to adjust the orientation of components, for example to orient the bubble generation means such that the fluid delivery is done in a vertical orientation with the fluid driven from the bottom up, in order to utilize buoyancy and gravity to promote consistency in bubble parameters and to promote desirable bubble properties, for example homogeneity.

The bubble generating apparatus and processes of the present invention may employ adjustable fluid delivery flowrates, multiple fluid delivery cycles of varying fluid flowrates, and component orientation means in order to vary bubble parameters. For example, programmable, electromechanical variants of the devices may employ high flowrate fluid delivery through the bubble generation means, may reorient the bubble generation means vertically for flowrate cycles, and may vary fluid delivery flowrates and orientation in particular cycles to purge the bubble solution of undesirable by-products.

A purge cycle may involve a final, reduced flowrate fluid delivery cycle after bubble generation cycles. Larger, medically undesirable bubbles and foam are more buoyant than smaller, more medically useful bubbles less than ten microns in diameter. The undesirable large bubbles and foam may therefore be separated from the medical useful bubble solution through a timed cycle and controlled fluid delivery.

The bubble generating apparatus and processes of the present invention may employ alternating fluid delivery flowrate cycles in order to promote bubble concentration, homogeneity, and other desirable bubble characteristics, in a cost effective, efficient means.

For example, a high flowrate cycle may be alternated with a lower flowrate cycle and the fluid vessels in the bubble generating means may include a high burst pressure syringe to accommodate the high flowrate cycles without fluid leaks operatively connected to a conventional, lower-price commodity syringe for lower flowrate cycles.

For an alternate example, fluid vessels of differing geometries may be employed. A conventional three milliliter syringe may be operatively connected to a ten milliter syringe and the bubble fluid reciprocated back along a flow path at a similar linear actuation speed. This would induce a higher flowrate in the cycles where the larger, fluid vessel was actuated.

The bubble generating apparatus and processes of the present invention may employ a valve and fluid delivery system or a means to detach and re-attach additional fluid vessels in order to combine the bubble fluid with other fluids, for example therapeutic agents. Additional fluids may be combined with the bubble fluid pre, post, or during bubble generation cycles. An advantage would be to optimize the combining or intermixing of the bubbles with other agents. Pre-generation delivery of the bubble fluid with other fluids would optimize combining and mixing. If the shear stress required for bubble generation might harm a particular agent, for example a biotherapeutic gene construct, the additional fluid containing the agent could be delivered after higher flowrate bubble generation cycles and intermixed at lower flowrates, or the additional fluid could be delivered post generation.

The bubble generating apparatus and processes of the present invention may employ means to adjust the orientation of components at high speeds, for example to rotate fluid vessels about a fixed access at a high speed in order to centrifuge the bubble fluid. This will promote separation within the bubble fluid in accordance with density. A centrifuge cycle could be used to produce high bubble concentrations, or to separate therapeutic or other agents combined with gas bubbles with therapeutic or other agents in the bubble fluid carrier liquid. Additional carrier liquid could be added to the bubble fluid post-separation. This would be useful for targeted or toxic therapeutic agents where the combining of such agents with the bubbles and the removal or reduction of such agents from the bubble carrier liquid would promote treatment efficacy.

Using bubble generating apparatus and processes of the present invention, bubble size or persistence may be adjusted in vivo. Different gas types are more soluble in the bloodstream and bubbles with high density gas will persist longer in vivo.

Bubbles with less dense gas types, for example air, could be used to create transient in vivo bubbles that permit ultrasound image enhancement and with prompt clearance from the body. Bubbles with denser gas, for example a perfluorocarbon, could be used to create more persistent bubbles in vivo.

Bubbles with a mixture of low and high density gas types, for example, an air and a perfluorocarbon (pfc) gas mixture, or pfc's of different densities, could be used to create bubbles that shrink in vivo and produce small, low micron or nano sized bubbles. Small bubbles may be medically useful for imaging or disruption with high frequency ultrasound and special Focused ultrasound equipment. Smaller bubbles may also be desirable for particular anatomical regions.

For example, nano sized bubbles may permit effective imaging with special high frequency fifteen to thirty (15-30) MHz ultrasound.

Using bubble generating apparatus and processes of the present invention, bubble parameters, for example the ultrasound disruption threshold of the bubbles, may be varied.

The term "ultrasound disruption threshold" is intended to include the required ultrasound energy delivered to the bubbles in order to induce desired therapeutic or imaging effects. Such effects may include, for example, that the bubbles resonate or are destroyed in order to increase cell permeabilization, that the bubbles combined with drugs rupture in order to release drugs locally on demand, and that the acoustic response properties of the bubbles may be varied. Ultrasound disruption threshold is intended to include the required ultrasound energy delivered to the bubbles to induce sonoporation, inertial and non-inertial cavitation, and acoustic activation.

Ultrasound energy is typically described as a combination of parameters including intensity, which may be defined in terms of mechanical index, pressure, decibels, or energy per surface area, the ultrasound frequency, pulse mode, pulse repetition frequency, pulse duration, and other parameters.

The predominant bubble characteristic that affects the ultrasound disruption threshold is the bubble shell and in particular the shell thickness.

Using bubble generating apparatus and processes of the present invention, the bubble shell characteristics may be adjusted. An additive, for example a PEG or cholesterol coating may be combined with the shell components in order to increase the thickness of the bubble shell. Salt may be combined with the shell components, for example to enhance the surfactant properties of surfactant-based shells. Salt may also reduce bubble coalescence after generation, an undesirable process as smaller bubbles with a consistent size distribution are typically more medically useful.

Using bubble generating apparatus and processes of the present invention, bubbles may be combined with agents, for example therapeutic agents and targeting agents.

The potential benefits of combining therapeutic, targeting, or targeted therapeutic agents to medical bubbles are to permit local delivery to an area of interest, for example a tumour, increased drug uptake and efficacy, reduced drug dose, reduced drug side effects, reduced immune system interference, for example the removal of a drug from the blood by the immune system, and real-time monitoring of drug delivery through ultrasound contrast imaging.

Bubbles may be combined with therapeutic, targeting, or targeting therapeutic agents proximal to the patient procedure site, for example in a hospital pharmacy, or order to permit the separate shipping and storage of such agents. Biotherapeutics and bio-targeting agents may require special handling and storage conditions whereby there are advantages to combining such entities with bubbles prior to patient infusion.

Bubbles may be combined with therapeutic, targeting, or therapeutic targeting agents, for example biotherapeutic agents, anchors, or linking agents, prior to or during bubble generation. The bubbles may be directly combined with the therapeutic or targeting agents during generation or by means of a staged procedure whereby, for example, cross linkers or anchors may be combined with micro or nano bubbles during generation and the therapeutic or targeting agent combined with the cross linkers and bubbles post bubble generation.

The advantage of combining therapeutic agents or anchors or cross linkers to bubbles during generation is to increase the drug payload per bubble through dynamic resizing of the bubbles during generation and to ensure even drug distribution throughout the bubble solution through the generation mixing process.

Dynamic resizing is an observed phenomenon of the bubble generating apparatus and processors of the present invention that, at the time of generation, the bubbles are of a larger size and then shrink and stabilize at smaller, more medically useful sizes. For example, at generation bubbles in the twenty to forty (20-40) micron diameter range may encapsulate drugs or be combined with anchors or cross linkers. Within seconds the bubbles may shrink and stabilize to one to four (1-4) micron or nano sizes with a higher quantity of drug encapsulated or a higher concentration of anchors or linkers per bubble surface area than would be accomplished through encapsulating drugs or combining anchors or therapeutic agents to bubbles after generation at smaller, stable bubble sizes.

Therapeutic agents may be combined with bubbles through the encapsulating of the drug in the bubble. For those variants, untargeted-manual delivery could be employed, whereby imaging ultrasound could be used to locate and track the bubble and drug combinations in the bloodstream and then to disrupt the bubbles at the area of interest in order to achieve local drug delivery. This untargeted-manual delivery method could also be used with those variants where the drug is bound to the bubble shell via an anchor, linker and/or spacer.

For variants used to encapsulate therapeutic agents within the bubbles, therapeutic agents which are oil based, hydrophobic, amphiphilic, soluble in oil, or possessing surfactant-like qualities, may be readily encapsulated during generation with surfactant based bubbles.

For variants used to bind therapeutic, targeting, or targeted therapeutic agents to the bubble shell an anchor may be incorporated within the shell. A linker may then be bound to the bubble shell with a therapeutic, targeting, or targeted agent or a spacer arm may be bound to the bubble shell and the targeting agent bound to the spacer. The advantage of spacers would be to increase the targeting success to the area of interest.

For example, a biotinylated anchor may be incorporated within the bubble fluid, for example within a gas, chemical, and carrier liquid solution, and bubble generation would then incorporate the anchor within the bubble shells. A centrifuge purge may then be required to separate unincorporated anchors from the bubble carrier liquid. A generic linker such as avidin, neutravidin, streptavidin, or HaloTag may then be bound to the bubbles, permitting binding of a biotinylated protein, ligand, or drug. Biotinylation can be done on carboxyl, sulfhydryl, and amine groups Targeting agents, such as ligands, receptors, fusion proteins, and others, may be combined with the bubbles in order to create targeted therapies or targeted diagnostic agents.

For therapy, the drug and targeting agents may be combined with bubbles, infused in a patient, and these preferentially gather at the disease site. Ultrasound energy could then be used to disrupt the bubbles and to release the drug locally. The ultrasound could also be used to disrupt the bubbles, to induce acoustic activation, sonoporation, inertial cavitation, and the like, in order to permeabilize tissue so that the drug is released locally and the cellular uptake and efficacy of the drug enhanced.

For targeted diagnostics, a combination of targeting agents and bubbles could be infused within a patient. These would preferentially gather at the disease site and ultrasound imaging enhanced, through the echogenicity of the bubbles, in order to diagnose conditions not visible through conventional ultrasound imaging. For example, a molecule that preferentially attached to liver cancer could be combined with bubbles and infused into people with hepatitis who have a higher risk of liver cancer. If tumours were present but too small to be detectable with conventional ultrasound, the bubbles and targeting agent would preferentially gather at these small tumour and be detectable with the ultrasound so that treatment could commence during the earliest, most treatable stage of the disease.

Using methods and medical devices of the present invention targeted diagnostics could also be used to enhance therapy. The bubbles combined with targeting agents could be infused in order to accumulate at the disease site. Once a sufficient concentration of bubbles were administered a systemic drug could be administered and the bubbles disrupted by ultrasound. This method would permit localized permeabilization and increased drug uptake at the disease site.

The bubbles could also be combined with ferrous particles so that they would provide image enhancement for ultrasound and MRI. This could be useful for research and clinical applications where multiple imaging modalities are preferred.

Using methods and medical devices of the present invention, bubbles may enhance therapeutic agent efficacy and safety in a variety of means.

A therapeutic agent or agents may be administered systemically, for example conventional intravenous administration of chemotherapy drugs, and the bubbles delivered locally, for example to a tumour using established ultrasound-guided needle or catheter procedures. The ultrasound parameters may then be modified in order to disrupt the bubbles and to permeabilize tissue in an area of interest, for example a tumour, to increase drug uptake and efficacy. Such a method may improve therapeutic results with a conventional drug dose or may improve therapeutic results with a reduced drug dose in order to lessen undesired side effects.

A therapeutic agent or agents and bubbles may both be administered locally, for example to a tumour using established ultrasound-guided needle or catheter procedures, and the ultrasound parameters modified in order to disrupt the bubbles and to permeabilize tissue in an area of interest, for example a tumour, to increase drug uptake and efficacy.

A therapeutic agent or agents and bubbles may both be administered systemically and special Focused ultrasound used to locally sonicate the area of interest, for example a tumour, to increase cell permeability and drug uptake and efficacy.

A therapeutic agent or agents and bubbles may be combined and administered either systemically or locally and ultrasound used to disrupt the bubbles and hence deliver drugs at an area of interest or to deliver the drugs and to permeabilize cells and hence increase drug uptake at the area of interest.

A therapeutic agent or agents and bubbles may be administered in a multiplicity of doses. For example, a therapeutic agent may be administered systemically and repeat doses of bubbles administered locally to an area of interest, and ultrasound used to image and verify local delivery and then to disrupt the bubbles and hence permeabilize cells and increase drug uptake and efficacy.

Using methods and medical devices of the present invention, bubbles may be infused within a patient and used to enhance therapies that do not require therapeutic agents or drugs to be administered to the body. For example, the bubbles may be used to accelerate the heating cycle of high intensity frequency ultrasound (HIFU) tumour ablation treatments, reduce treatment duration, and thus reduce patient trauma and expand potential applications. The bubbles may be used to reduce the energy required for ultrasound systems designed to lyse fat cells through cavitation. The bubbles may also be administered to tumours to enhance radiation treatments such as the neo-adjuvant treatment of breast cancer where ionizing radiation is used to reduce tumour size prior to surgery in order to improve the odds of a successful surgical outcome and to reduce patient trauma and scarring.

Using methods and medical devices of the present invention, bubbles may be infused within a patient and used to characterize tumour blood flow prior to, during, or after treatments in order to monitor and adjust treatment efficacy and to minimize effects to healthy tissue. Tumour treatments include radiotherapy using external beam or brachytherapy, thermal ablation techniques, for example radiofrequency heat probe ablation, high intensity frequency ultrasound (HIFU) tumour ablation, MRI guided Focused ultrasound (MRgFUS) ablation, direct or targeted chemotherapy treatments, or cryoablation techniques.

Doppler ultrasound detection of bubbles could be used to monitor tumour blood flow which relates to treatment efficacy. For example, for treatment regimes requiring repeated external beam radiotherapy doses this would permit real time adjustment of the number of doses, dose intensity, and targeting precision. For brachytherapy treatments this would permit real time adjustment of radioactive seed location and treatment duration.

It is to be appreciated that reference to a "device" of the present invention may be understood to include an "apparatus" or "assembly", which may be incorporated into systems with suitable adaptations.

It is also to be appreciated that the devices of the present invention may be used in a variety of applications, including medical diagnosis, image guided intervention, treatment, surgery, and the like, and also may be used in a similar fashion in veterinary applications and in animal research applications with suitable modifications.

The term "needle" is intended to include any hollow, slender instrument that may be manipulated to puncture or be inserted or otherwise probe tissues, organs, cavities, or the like. The needle may be used to introduce material into or remove material from a patient or to perform other therapeutic or diagnostic functions. The term needle is intended to include rods or wire-like medical instruments, cannulas, probes, tubes and lumens, stylets, and the like.

The term "patient" may be any suitable animal, including humans and other mammals.

The term "catheter" is intended to include any flexible surgical instrument for the introduction of fluids into the body, including catheters for repeat dose drug delivery such as hickman lines, PORTACATH™ lines and the like.

The fluids container may be any suitable vessel to contain gases or liquids, such as syringes, gas tanks, a central, building-supply, fluid source that may be connected to the device via fluid conduit, and the like.

The fluid delivery means may be a syringe plunger actuated manually, a syringe pump, an electromechanical means with which to actuate syringe plungers, a variable speed fluid transfer pump, a peristaltic pump, the regulated release of compressed gas, or other suitable means to supply fluids. The delivery means may also be driven manually or by mechanical means such as compression or extension springs, or other mechanical methods, by electromechanical means such as an electric motor, solenoid drive, or other electromechanical means, or by pneumatic or hydraulic means.

Over all, it is to be appreciated that terms used herein are to be interpreted and understood expansively and not strictly.

In summary of its process aspect the present invention discloses a method of generating from bubble fluid medically useful bubbles of medically desirable size, size distribution, concentration and homogeneity comprising the steps of reciprocally driving the bubble fluid through and between spatially separated, first and second fluid vessels that are connected in a flow path via a bubble generating module in such a way that the bubble fluid is first driven half a reciprocal cycle in a first direction along the flow path upwardly vertically through one of the spatially separated, first and second fluid vessels into the other one of the spatially separated first and second fluid vessels via the bubble generating module, and is then driven the other half reciprocal cycle in a second direction along the flow path opposite to the first direction upwardly vertically through the other one of the spatially separated first and second fluid vessels back into the first one of the first and second fluid vessels via the bubble generating module; repeating for a predetermined number of reciprocal half cycles said reciprocally driving fluid step so as to produce said medically useful bubbles of said medically desirable size, size distribution, concentration and homogeneity together with undesirable components including foam and larger undesirable bubbles; and removing the undesirable components from the medically useful bubbles of medically desirable size, size distribution, concentration and homogeneity. The predetermined number of reciprocal half cycles is a number selected from the group of numbers consisting of zero (0), even whole integers and odd whole integers. In one preferred embodiment, the bubble generating module consists of a single capillary tube and single mix chamber of comparatively smaller and comparatively larger cross-section.

In one embodiment where the spatially separated, first and second fluid vessels are in-line vessels and bubble generating module that are carried by a disposable cartridge, the reciprocally driving fluid step through and between the in-line vessels and bubble generating module of said disposable cartridge includes the step of inverting the disposable cartridge between each half reciprocal cycle of said reciprocally driving step, and, when the predetermined number of reciprocal half cycles is an even whole integer, the repeating said reciprocally driving fluid step through the in-line vessels and bubble generating module of said disposable cartridge includes the step of inverting the disposable cartridge between each half reciprocal cycle of each said even whole integer number of times said reciprocally driving fluid step is repeated.

In another embodiment where the spatially separated, first and second fluid vessels are connected in a flow path via a bubble generating module that are arranged in a U-shape in a disposable cartridge, the bubble generating module is arranged to form the base of the U-shape and each of the first and second fluid vessels is arranged to form another one of its legs which are each vertically oriented when the bubble generating module is horizontally orientated.

The bubble fluid includes preselected shell and globule components selected to provide bubbles useful for acoustic imaging; for one of sonoporation, inertial and non-inertial cavitation and acoustic activation, and may include a shell additive to control ultrasound disruption threshold useful for one of sonoporation, inertial and non-inertial cavitation and acoustic activation; for targeted delivery or untargeted-manual delivery, they may include at least one of an anchor, linker and spacer; and/or may include preselected shell and globule components selected to provide bubbles useful for therapy, such as fat lysing, HIFU for tumor ablation and radiation therapy.

In summary of its apparatus aspect the present invention discloses a medical bubble generator device producing medically useful bubbles of medically desirable size, size distribution, concentration and homogeneity, comprising a base station; a cradle rotatably mounted to the base station; a disposable cartridge removably mounted to the cradle; said cradle including first and second fluid delivery means mounted for rotation with said cradle; said cartridge including first and second fluid vessels and a bubble generating module intermediate said first and second fluid vessels that are connected along a flow path; and said cradle adapted to selectively orient the removable cartridge and said first and second fluid delivery means adapted to controllably move fluid through the first and second fluid vessels of the removable carriage when it is in a selected orientation so as to produce said medically useful bubbles of medically desirable size, size distribution, concentration and homogeneity in said removable, disposable cartridge.

In one presently preferred embodiment, the first and second fluid delivery means are first and second linear actuators, and said cradle and linear actuators in alternative embodiments are adapted to be manually responsive or adapted to be responsive to a programmable controller to selectively orient the removable to controllable move fluid through the first and second fluid vessels of the removable cartridge when it is in a selected orientation so as to produce said medically useful bubbles of medically desirable size, size distribution, concentration and homogeneity in said removable, disposable cartridge.

In one presently preferred embodiment, the rotatable cradle and linear actuators are operated to provide at least one cycle of reciprocating flow such that each cycle fluid is caused first to flow in one direction along said flow path out of one and into the other one of the fluid vessels via the bubble generating module of said removable, disposable cartridge and then caused to flow along said flow path of said removable, disposable cartridge in a second direction counter to and opposing said first direction out of the other one and into the first one of the fluid vessels via the bubble generating module in such a way that first the one and then the other of the first and second fluid vessels of the removable, disposable cartridge is vertically oriented when fluid is caused to flow in the first and second directions.

In one embodiment the first and second fluid vessels and intermediate bubble generating module are in-line first and second fluid vessels and intermediate bubble generating module and said rotatable cradle is operated to invert the removable, disposable cartridge between each half cycle of a reciprocal cycle.

In another embodiment the first and second fluid vessels and intermediate bubble generating module are arranged in a disposable cartridge in a U-shape, wherein the bubble generating module forms the base of the U-shape and each of the first and second fluid vessels forms another one of its legs which are each vertically oriented when the bubble generating module is horizontally orientated.

At least one of said linear actuators may be operated to so move fluid along said flow path of said removable, disposable cartridge as to purge unwanted components including foam and undesirably large bubbles from said medically useful bubbles of medically desirable size produced in said removable, disposable cartridge.

For an initial reciprocal cycle the cradle and/or linear actuators may be operated to reciprocally move fluid along said flow path of the removable, disposable cartridge in the first and second directions at first and second comparatively high and comparatively low speeds to avoid damaging sensitive fluid components, the comparatively low speed set by a speed threshold beyond which sensitive fluid components may be damaged, and may be operated for at least one additional reciprocal half cycle to move fluid along said flow path of the removable, disposable cartridge in at least one the first and second directions at speeds below the speed threshold for damaging sensitive fluid components to produce said medically useful bubbles of medically desirable size, size distribution, concentration and homogeneity.

The cradle may be operated to so rotate said removable cartridge as to increase the concentration of said bubbles produced therein by a centrifuge action and at least one of said linear actuators may be operated to purge unwanted components from said increased concentration bubbles.

In addition to said medically useful bubbles, unwanted components may be contained in said removable cartridge, and the cradle may be operated to so rotate said cartridge as to separate the unwanted components from said medically useful bubbles by a centrifuge action.

The first and second fluid vessels may be comparatively expensive and comparatively inexpensive first and second comparatively high and comparatively low burst pressure syringes.

For at least one cycle reciprocating flow along said flow path may be accomplished at a predetermined, comparatively high speed, wherein the first and second fluid vessels have a bore size, wherein said linear actuators have a maximum speed, and wherein a combination of actuator speed and bore size is selected such that comparatively larger bore sizes are selectively combined with comparatively slower linear actuator speeds to provide said predetermined, comparatively high speed.

The foregoing summarizes some of the principal inventive apparatus and process aspects of the medical microbubble generation of the present invention and some of its advantageous features. The invention may be further understood by the description of the presently preferred embodiments, in conjunction with the drawings, which now follow.

BRIEF DESCRIPTION OF THE DRAWINGS

The accompanying drawings illustrate presently preferred embodiments of the invention and, together with the description that follows, serve to further explain the principles of the invention.

FIGS. 1D-1E depict an alternate U-shaped disposable, cartridge.

DETAILED DESCRIPTION OF THE PRESENTLY PREFERRED EMBODIMENTS

Reference will now be made in detail to various suitable embodiments including a presently preferred embodiments of the invention as illustrated in the accompanying drawings. It will be understood that this description is exemplary and is to assist in understanding the invention and the principles of operation.

Figure 1A:
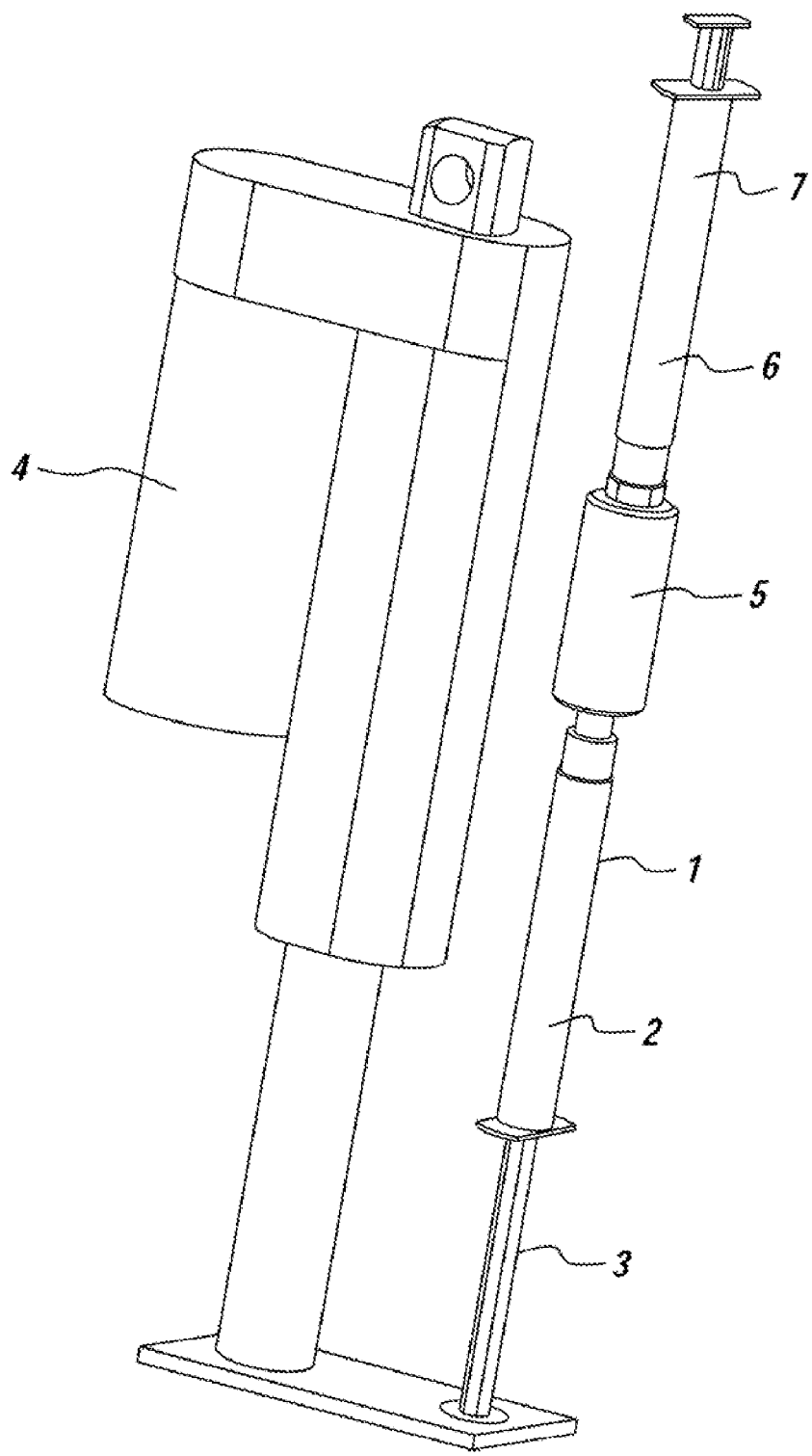
FIG. 1A depicts a microbubble generating device that employs an electromechanical actuator to generate microbubbles of varying sizes.

FIG. 1A depicts a microbubble generating device that employs an electromechanical actuator to generate microbubbles of varying sizes.

A generator syringe 1 is preloaded with a surfactant saline solution 2. The generator syringe plunger 3 is withdrawn in order to infuse a quantity of air within the generator syringe 1 to achieve a desired liquid to gas ratio. The generator syringe 1 may also be preloaded with a suitable microbubble forming gas such as, but not limited to, perfluorocarbons, sulfur hexafluoride and/or osmotic agents such as nitrogen.

The surfactant solution 2 may be comprised of a number of suitable, commercially available surfactants, for example detergents, stearic or polmetic acid, or micelle-based surfactants, in a sterile saline, a phosphate buffered saline, deionized water, or other liquid suitable for injecting within the body. A plurality of surfactants, for example a Span (60) and Tween (80) combination, may be used. The surfactants may be melted, crushed, heated, stirred, mixed, or agitated within the liquid in order to ensure adequate solubility or distribution. The surfactant solution may require additional heating or agitation immediately prior to use. Agitation may be achieved by manual, mechanized, ultrasonic, or other suitable means. The solution may contain other additives to adjust viscosity, promote bioadhesion of the bubbles, or enhance effectiveness of a particular therapeutic agent.

A pneumatic, electromechanical or other actuator 4 and generator assembly 5 is connected to the generator syringe 1. The syringes 1, 7 and generator are arranged as an in-line disposable cartridge.

The actuator 4, driven by a programmable control system (not shown), is used to drive the syringe plunger 3 in order to infuse the surfactant solution 2 and gas mixture into the generator assembly 5 at a controlled flow rate Microbubbles are formed in the generator assembly 5 through an in-line flow technique and a microbubble solution 6 is produced and infused into a microbubble syringe 7 connected by an adaptor. In different embodiments of the FIG. 1 device, reciprocation through the generator 5 may and may not be employed.

Figure 1B:
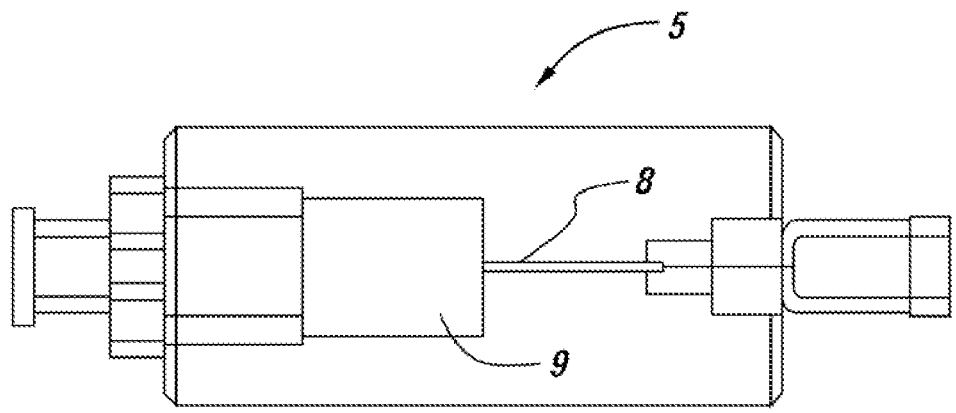
FIGS. 1B-1C depicts cross-sectional views of alternate bubble generator modules.
Figure 1C:
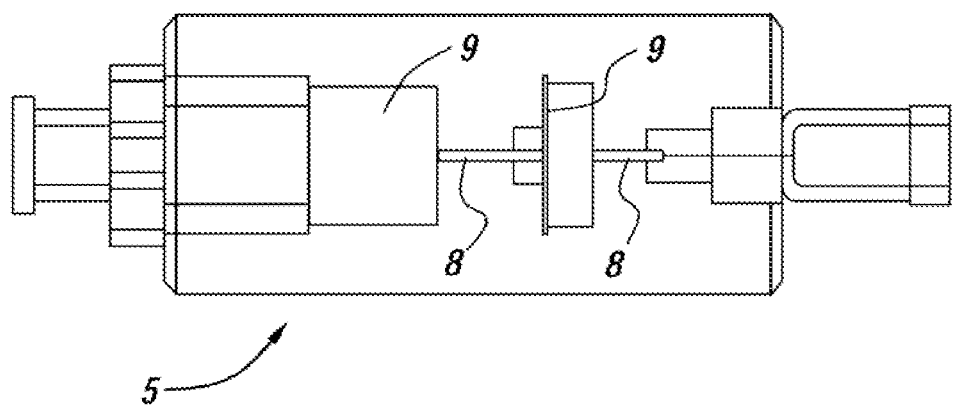

FIGS. 1B-C depict cross-sectional views of different generator assembly embodiments.

The generator assembly generally designated 5 is comprised of one set or a series of capillary tubes 8, mix chambers 9, and adaptors (not shown), which may be contained within an outer casing (not shown). FIG. 1B depicts an in-line, single capillary tube and single mix chamber system; FIG. 1C depicts an in-line two-stage system. Of course, more than two stages could be employed.

The number of capillary tubes and mix chambers arranged in series may range from one (1) of each to eight (8) of each or more. The inner diameter of the capillary tubes may be in the order of fifty (50) to one thousand (1000) microns with three hundred (300) microns typical. The length of capillary tubing may vary, for example with a first tube (0.5) to fifteen (15) cm in length and subsequent tubes one (1) to ten (10) cm in length. The mix chamber geometry may vary, with an inner diameter of (0.2) centimeters up to two (2) centimeters, with (0.5) centimeters typical, and a length of (0.05) centimeters up to five (5) centimeters, with one (1) centimeter typical. The capillary tubes may be arranged in a straight line or may be offset to promote the mixing of bubbles and liquid in the mix chambers.

The capillary tubes and mix chambers may be fabricated in a variety of methods using a variety of materials. Material selection would permit sterilization of interior surfaces contacting the surfactant solution that is to be infused within a patient.

Stainless steel medical needles cut to length may be used to form the capillary tubes. The mix chambers may be machined from sections of plastic tubing or bar stock, from material such as acrylic or Teflon, with a through hole drilled within which to fit the capillary tubes. Epoxy may be used to leak proof the mated tubing sections. Syringe adaptors may be standard leak tight adaptors such as Luer-lok.

FIGS. 1D-1E depict an alternate U-shaped disposable, cartridge.

The U-shaped disposable, cartridge generally designated at 10 includes a bubble generator module 5 that includes one set (or a series) of capillary tubes 8, mix chambers 9, and adaptors, not shown. The adaptors are located on the same side of the bubble generator module 5 and allow the generator syringe 1 and microbubble syringe 7 to be attached to one side of the bubble generator module 5. The spatially separated syringes 1, 7 are connected in a flow path via bubble generating module and are arranged in a U-shape in the cartridge 10, where the bubble generating module 5 is arranged in the cartridge to form the base of the U-shape and each of the syringes is arranged in the cartridge to form another one of the legs of the U-shape. The syringe legs are each vertically oriented when the bubble generating module 5 is horizontally orientated.

Figure 2A:
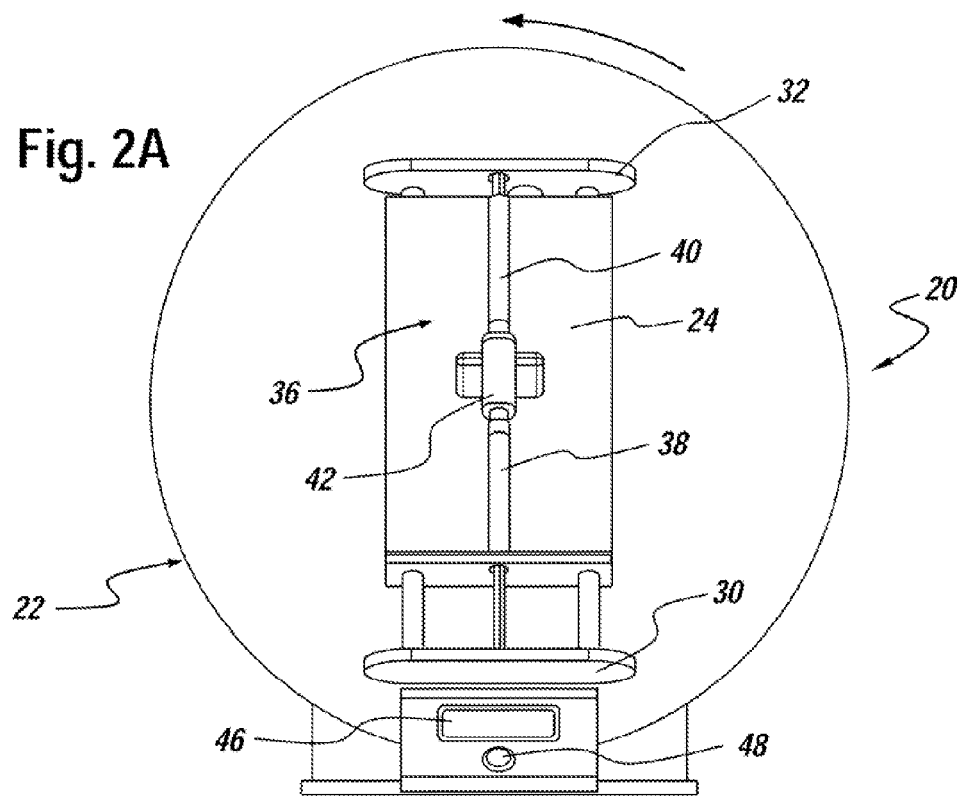
FIGS. 2A, 2B depict one presently preferred embodiment of the medical microbubble generation apparatus in accord with the present invention.
Figure 2B:
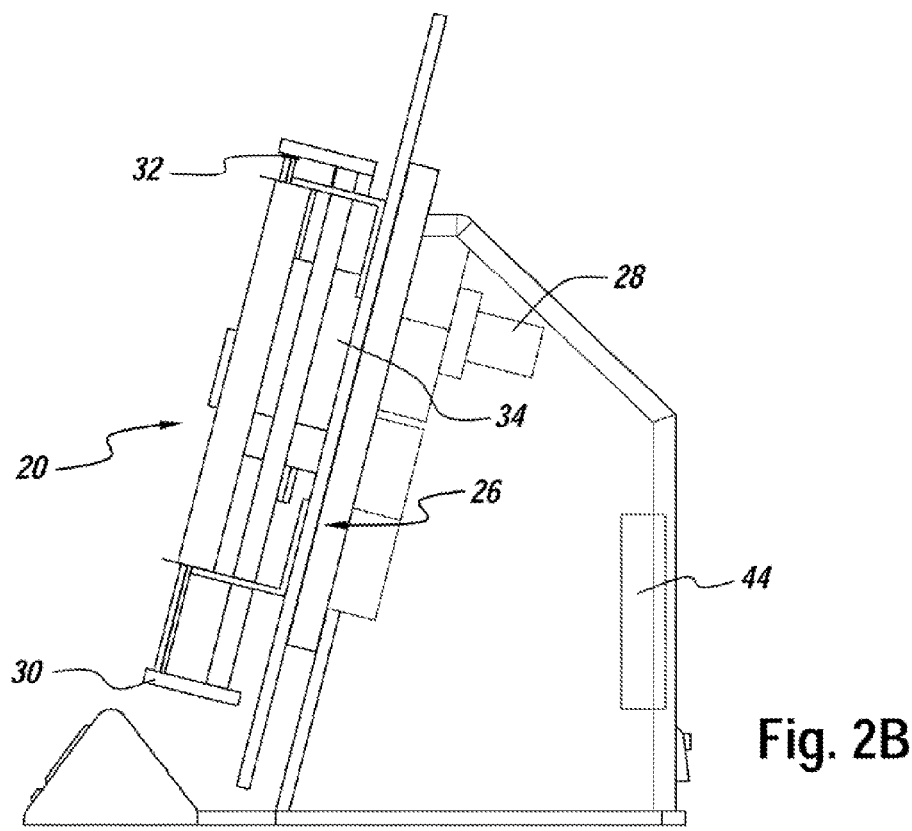

FIGS. 2A, 2B depict one presently preferred embodiment of the microbubble generating device of the present invention.

The microbubble generating device 20 includes a base station generally designated 22 and a cradle 24 rotatably mounted to the base station 22 via rotary actuation assembly generally designated 26 operatively connected to motor 28. The cradle 24 includes linear actuators 30, 32 mounted for rotation with the cradle 24. The linear actuators 30, 32 are controllably displaced by motor 34 operatively coupled to the linear actuators 30, 32. An in-line disposable cartridge generally designated 36 is removably mounted to the cradle 24. The disposable cartridge 32 includes in-line first and second syringes 38, 40 having syringe plungers that are connected in a fluid flow path via an intermediate bubble generating module 42. The syringe plungers of the first and second syringes 38, 40 are driven by the associated one of the linear actuators 30, 32. Programmable controller 44 having graphical user interface (GUI) 46 and input buttons 48 is operatively coupled to the motors 28, 34. The controller 44 selectively rotates the cradle 32 to controllably orient the cartridge 36 and selectively drives the actuators 30, 32 to controllably move fluid through the first and second syringes 38, 40 of the removable cartridge 36 when it is in a selected orientation. Either the actuation plates 30, 32 are held stationary while the microbubble generation assembly holder/cradle 24 is actuated or the holder/cradle 24 is stationary while the actuation plates 30, 32 are actuated. In the illustrated embodiment, the linear actuators 30, 32 are driven together. They may be driven separately in an alternate embodiment, not shown.

The microbubble generating device 20 is loaded by placing the disposable, removable cartridge 36 having in-line generation syringe 38 preloaded with bubble fluid and an empty microbubble syringe 40 connected in a flow path via an intermediate bubble generating module 42 into the rotatable cradle 24 of the base station 22. Once loaded, the user is prompted by the GUI 46 to press the input/"start" button 48 and the controller 44 selectively rotates the cradle 32 to controllably orient the cartridge 36 and selectively drives the actuators 30, 32 to controllably move fluid through the first and second syringes 38, 40 of the removable cartridge 36 when it is in a selected orientation under program control. Of course, the cradle 24 and actuators 30, 32 could be operated manually without departing from the inventive concepts.

Figure 3:
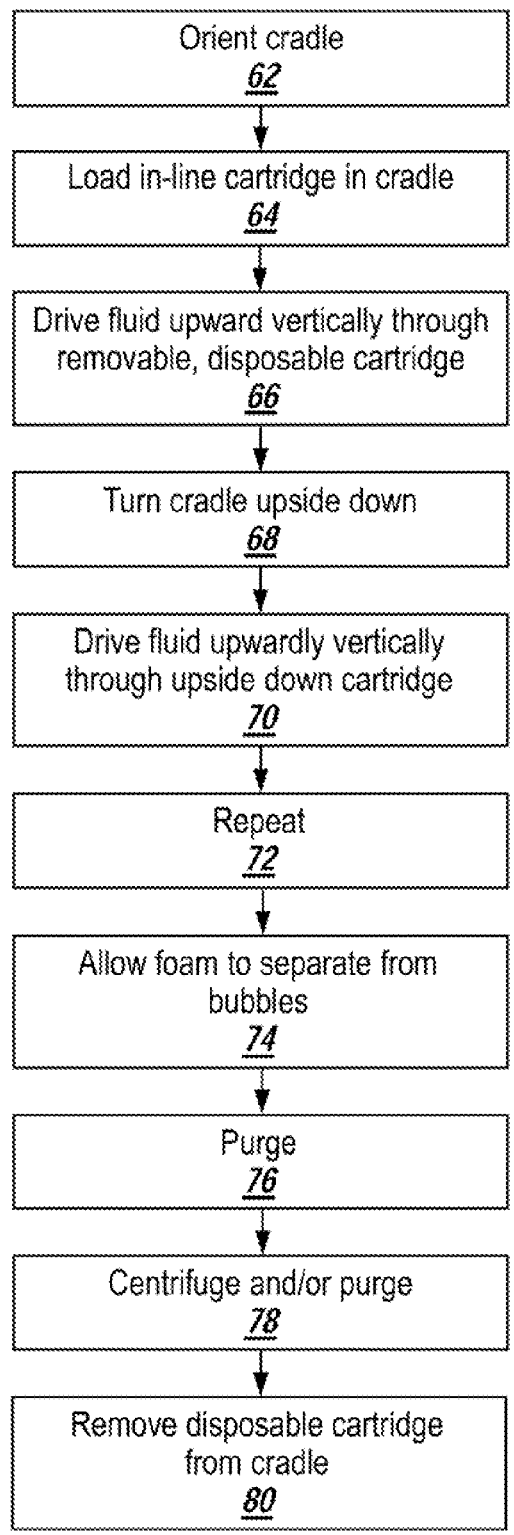
FIG. 3 is a flow chart useful in explaining one medical microbubble generation process in accord with the present invention.

Referring now to FIG. 3, generally designated at 60 is a flowchart useful in explaining one medical bubble generation process in accord with the present invention. In a first step 62, the cradle is rotated to the starting position.

As shown by block 64, the in-line cartridge is removably mounted to the rotatable cradle.

As shown by block 66, a bubble fluid preloaded in one of the fluid vessels or generation syringe, by way of example the lower syringe, is driven upwardly vertically through the generation syringe and into the other fluid vessel, or empty upper syringe, via the bubble generation module.

As shown by block 68, the cradle is then rotated so that the cartridge is turned upside down.

As shown by block 70, the associated actuator is then operated to drive the fluid upwardly vertically through the lower syringe and back into the upper syringe via the bubble generating module.

As shown by block 72, the steps 68, 70 are repeated for a predetermined number of reciprocal half cycles in order to controllably produce medically useful microbubbles of medically desirable size, size distribution, homogeneity and concentration in dependence on the number of reciprocal half cycles employed for any given bubble fluid. Depending on the medical application and bubble fluid employed the predetermined number of reciprocal half cycles is a number selected from the group of numbers consisting of zero (0), even whole integers and odd whole integers.

As shown by block 74, after the bubble fluid has been reciprocated to and fro through the bubble generation module a prescribed number of times to produce bubbles of medically useful size, size distribution, concentration and homogeneity, any unwanted components, that may include foam and larger, medically undesirable bubbles, are allowed to separate from the medically desirable microbubbles.

As shown by block 76, after the unwanted components have been allowed to separate, the linear actuator is operated to purge the unwanted components from the syringe containing the medically desirable microbubbles together with the undesirable components leaving only the medically useful microbubbles of medically desirable size, size distribution, concentration and homogeneity.

The undesirable components will rise to the top of the cartridge. When, for example, the undesirable components are purged from the top fluid vessel, the corresponding actuator is driven at a comparatively slower speed than the speed used for bubble generation in order to move the microbubbles into the bubble generation module. The length of travel is selected to move the medically useful bubbles through the bubble generation module into the bottom syringe. Of course, the purge cycle could be completed bottom-up; the corresponding actuator driven at slower speed than during bubble formation is caused to travel a distance selected to move the unwanted components into the bubble generation module, which then will act as a waste receptacle, leaving the medically useful microbubbles of medically desirable parameters in the lower syringe.

In practice, as detailed in the examples hereinbelow, it has been found that six (6) whole reciprocal cycles has produced optimized bubble parameters in these examples. In general, beyond a certain number of reciprocal half cycles no improvement in desired bubble characteristics has been observed. Generally, this number will be less than thirty (30) or so; typically four to six (4-6) whole reciprocal cycles have been found to be optimal.

As shown by block 78, one or more optional centrifuge and/or purge cycles may be employed depending on the medical application and in dependence on the composition of the bubble fluid and other fluid components or constituents.

As shown by block 80, the removable disposable cartridge containing medically useful microbubbles of medically desirable size, size distribution, concentration and homogeneity is then removed from the cradle.

Figure 4:
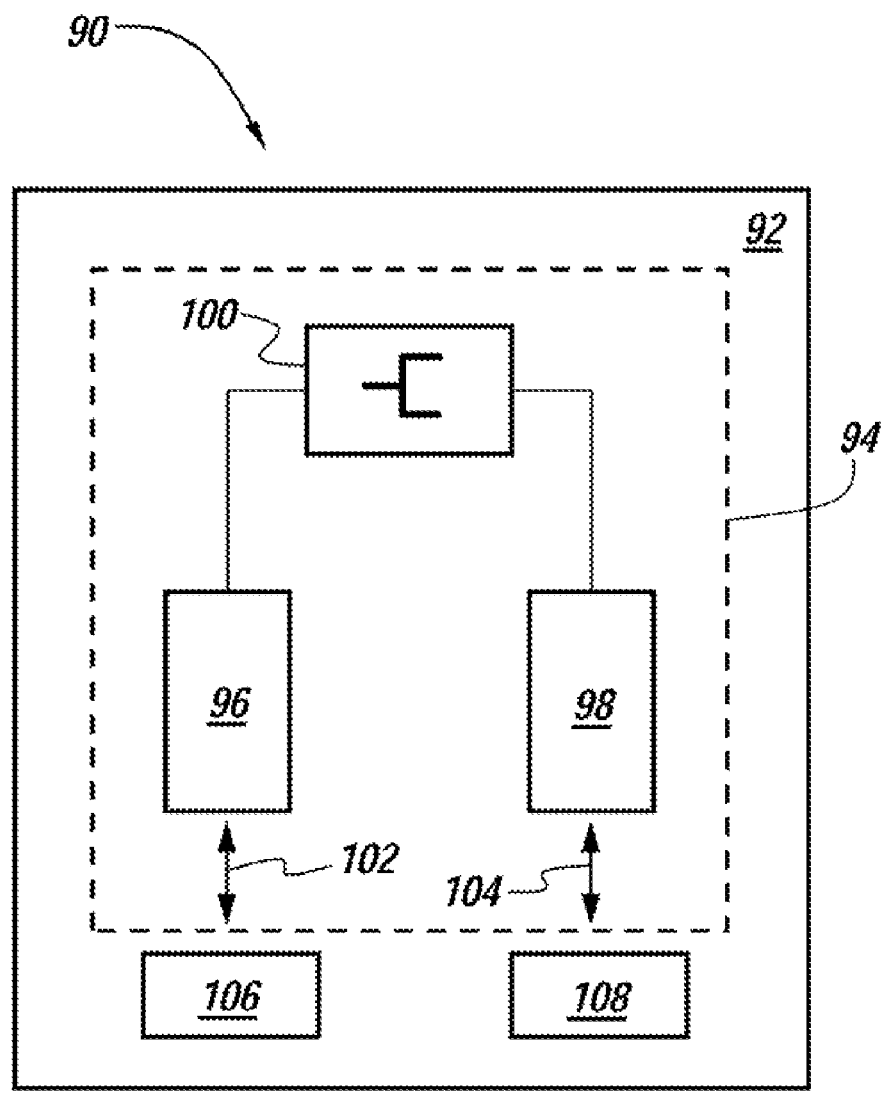
FIG. 4 depicts another presently preferred microbubble generation apparatus embodiment in accord with the present invention.

Referring now to FIG. 4, generally designated at 90 is a block diagram illustrating another embodiment of a medical microbubble generation apparatus in accord with the present invention. The microbubble generation apparatus 90 includes base station cradle 92 adapted to removably receive a disposable cartridge. A disposable cartridge schematically illustrated by dashed box 94 is removably received by the cradle 92. The disposable cartridge 94 includes first and second fluid vessels 96, 98 and intermediate bubble generating module 100 that are arranged in the removable, disposable cartridge 94 in a U-shape, where the bubble generating module 104 is arranged to form the base of the U-shaped cartridge and each of the first and second fluid muscles 96, 98 are arranged to form another one of it legs which are each vertically oriented when the bubble generating module is horizontally orientated. The bubble generating module 100 preferably consists of a single capillary tube and single mix chamber respectively of comparatively smaller and comparatively larger cross-section. The syringes 96, 98 include syringe plungers schematically illustrated by double-headed arrows 102, 104 that are respectively driven by linear actuators 106, 108. The actuators 106, 108 may be manually operated or operated in response to a programmable controller, not shown, without departing from the inventive concepts.

Figure 5:
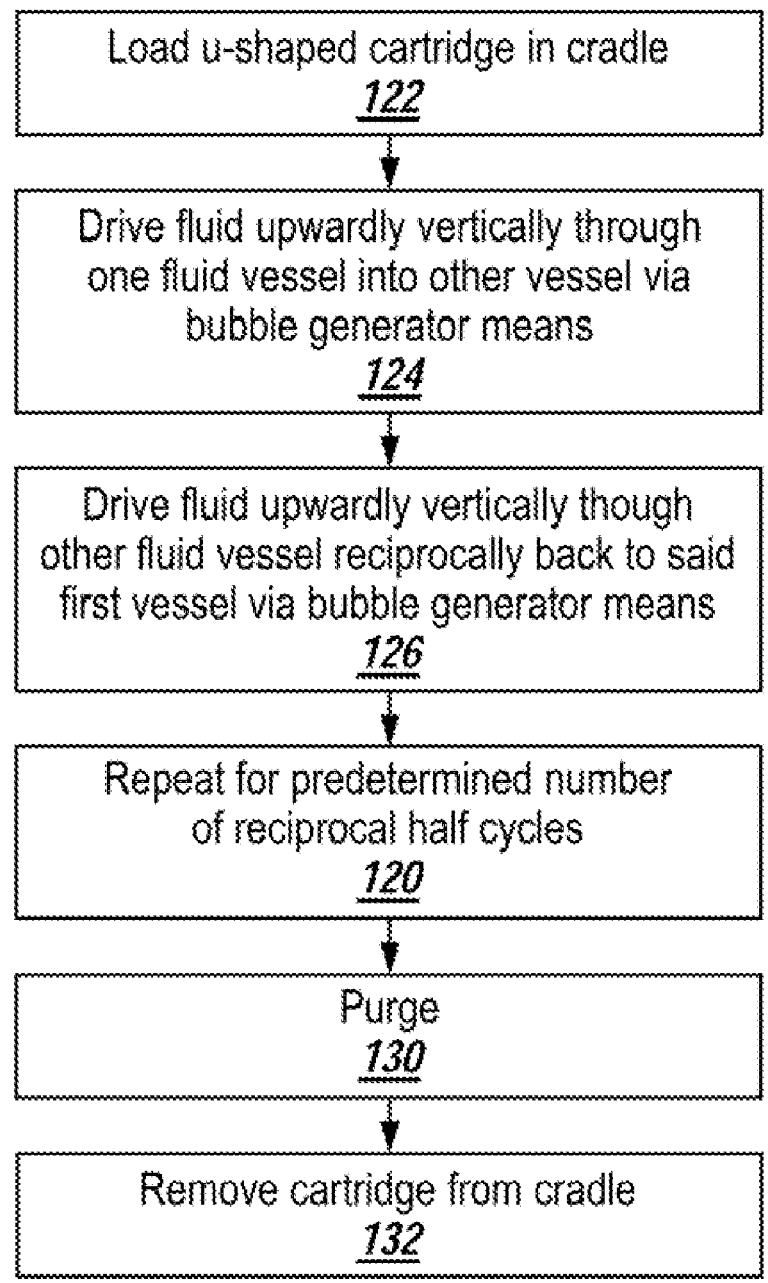
FIG. 5 is a flow chart useful in explaining a medical microbubble generation process variation in accord with the present invention.

Referring now to FIG. 5, generally designated at 120 is a flowchart useful in explaining a medical microbubble generation process variation in accord with the present invention. In a first step 122, the U-shaped cartridge is removably mounted in the cradle.

As shown by block 124, bubble fluid preloaded in one fluid vessel of the removable cartridge is driven upwardly vertically therethrough and into the other fluid vessel via the bubble generation module in one direction along the flow path.

As shown by block 126, the associated actuator is then operated to drive the fluid upwardly vertically through said other syringe and back into said one fluid vessel via the bubble generating module reciprocally back along the flow path.

As shown by block 128, the steps 124, 126 are repeated for a predetermined number of times in order to controllably produce medically useful microbubbles of medically desirable size, size distribution, homogeneity and concentration in dependence on the number of reciprocal half cycles employed for any given bubble fluid. Depending on the medical application and bubble fluid employed the predetermined number of reciprocal half cycles is a number selected from the group of numbers consisting of zero (0), even whole integers and odd whole integers.

As shown by block 130, after the bubble fluid had been reciprocated through the bubble generation module a prescribed number of times to produce bubbles of medically useful size, size distribution, concentration and homogeneity, any unwanted components that may include foam and larger bubbles are allowed to separate from the medically desirable microbubbles and the corresponding linear actuator is operated to purge the unwanted components from the syringe containing the medically desirable microbubbles together with the undesirable components leaving only the medically useful microbubbles of medically desirable size, size distribution, concentration and homogeneity.

As shown by block 132, the removable, disposable cartridge containing medically useful microbubbles (or nano bubbles) of medically desirable size, size distribution, concentration and homogeneity (and/or other key bubble parameters) is then removed from the cradle.

EXAMPLE A

Six (6) reciprocal cycles with a three (3) mL bubble fluid preload of two and one-half (2.5) mL liquid and one-half (0.5) mL of gas produced between one (1) and two (2) $(1-2)*10^8$ microbubbles per milliliter of one and one-half (1.5) µ diameter size that exhibit excellent size distribution and homogeneity. These bubbles have been found useful for ultrasound image enhancement and their ultrasound disruption properties have been found useful for sonoporation, inertial and non-inertial cavitation and acoustic activation. It may be noted, that during bubble generation, dynamic resizing has been observed.

EXAMPLE B

Six (6) reciprocal cycles with a three (3) mL bubble fluid preload of two and one-half (2.5) mL liquid and one-half (0.5) mL of a fifty/fifty (50/50) mix of pfc and air produced between one (1) and two (2) $(1-2)*10^8$ microbubbles per milliliter of one and one-half (1.5) µ diameter size that exhibited shrinkage to sub micron bubbles in vivo.

In both these examples, it was found that selecting the number of reciprocal half cycles and selecting the actuation speeds controllably varies the medically desirable bubble parameters. In general, for a given bubble fluid composition, the greater the number of reciprocal half cycles and the higher the fluid speed the greater the concentration and the more uniform the size distribution of the medical bubbles generated.

For a given number of cycles and fluid speed, selecting the bubble fluid composition and chamber geometry controllably varies the medically desirable bubble characteristics. It has been found, for example, that increasing the number of cycles allows simplification of the geometry of the bubble generator module. Single stage capillary tubes and single stage mix chambers have been employed to produce the results given in the examples above. This not only lowers costs and simplifies construction but has been found to promote batch to batch consistency.

While manual reciprocation (without linear actuators) through non-vertical syringes (or other fluid vessels) is a feasible means for generating microbubbles, it has been found that the combination of controlled vertical orientation and linear actuator controlled reciprocation produces microbubbles of superior medically desirable bubble characteristics and highly superior batch to batch consistency. The vertical orientation is a key to attainment of batch to batch consistency. It provides for more consistent layering in the bubble fluid components, which results in more consistent attainment of medically desirable microbubble parameters and allows precise purging of the undesirable components that may include foam and larger, medically undesirable microbubbles.

Many modifications of the presently disclosed invention will become apparent to those skilled in the art having benefitted from the instant specification without departing from the inventive concepts.

What is claimed is:

1. A method of generating from bubble fluid medically useful bubbles of medically desirable size, size distribution, concentration and homogeneity, comprising the steps of:

reciprocally driving the bubble fluid through and between spatially separated, first and second fluid vessels that are connected in a flow path via a bubble generating module in such a way that the bubble fluid is first driven half a reciprocal cycle in a first direction along the flow path upwardly vertically through one of the spatially separated, first and second fluid vessels into the other one of the spatially separated first and second fluid vessels via the bubble generating module, and is then driven the other half reciprocal cycle in a second direction along the flow path opposite to the first direction upwardly vertically through the other one of the spatially separated first and second fluid vessels back into the first one of the first and second fluid vessels via the bubble generating module;

repeating for a predetermined number of reciprocal half cycles said reciprocally driving fluid step so as to produce said medically useful bubbles of said medically desirable size, size distribution, concentration and homogeneity together with undesirable components including foam and larger undesirable bubbles; and removing the undesirable components from the medically useful bubbles of medically desirable size, size distribution, concentration and homogeneity.

2. The invention of claim 1, wherein said bubble generating module includes a capillary tube and mix chamber of comparatively smaller and comparatively larger cross-section.

3. The invention of claim 1, wherein said predetermined number of reciprocal half cycles is a number selected from the group of numbers consisting of 0, even whole integers and odd whole integers.

4. The invention of claim 1, wherein the spatially separated, first and second fluid vessels that are connected in the flow path via the bubble generating module are arranged in-line in a disposable cartridge.

5. The invention of claim 4, wherein said reciprocally driving fluid step through and between the in-line vessels and bubble generating module of said disposable cartridge includes the step of inverting the disposable cartridge between each half reciprocal cycle of said reciprocally driving step.

6. The invention of claim 4, wherein said predetermined number of reciprocal half cycles of said repeating step is an even whole integer; and wherein said repeating said reciprocally driving fluid step through and between the in-line vessels and bubble generating module of said disposable cartridge for said even whole integer number of times includes the step of inverting the disposable cartridge between each half reciprocal cycle of each said even whole integer number of times said reciprocally driving fluid step is repeated.

7. The invention of claim 1, wherein the spatially separated, first and second fluid vessels that are connected in the flow path via the bubble generating module are arranged in a U-shape in a disposable cartridge including legs and a base, wherein each of the first and second fluid vessels are arranged in the cartridge to form another one of its legs which are each vertically oriented when the base is horizontally orientated.

8. The invention of claim 1, wherein said bubble fluid includes preselected shell and globule components selected to provide bubbles useful for acoustic imaging.

9. The invention of claim 1, wherein said bubble fluid includes preselected shell and globule components selected to provide bubbles useful for one of sonoporation, inertial and non-inertial cavitation and acoustic activation.

10. The invention of claim 9, wherein said bubble fluid includes a shell additive to control ultrasound disruption threshold useful for acoustic activation.

11. The invention of claim 1, wherein said bubble fluid includes preselected shell and globule components selected to provide bubbles useful for targeted delivery.

12. The invention of claim 11, wherein said shell components include at least one additive to provide at least one of an anchor, linker and spacer useful for one of targeted delivery and untargeted-manual delivery.

13. The invention of claim 1, wherein said bubble fluid includes preselected shell and globule components selected to provide bubbles useful for therapy.

14. The invention of claim 13, wherein said therapy is one of fat lysing, HIFU for tumour ablation and radiation therapy.

15. A method of generating from bubble fluid medically useful bubbles of medically desirable size, size distribution, concentration and homogeneity, comprising the steps of:

reciprocally driving the bubble fluid through and between spatially separated, first and second fluid vessels that are connected in a flow path via a bubble generating module in such a way that the bubble fluid is first driven half a reciprocal cycle in a first direction along the flow path upwardly vertically through one of the spatially separated, first and second fluid vessels into the other one of the spatially separated first and second fluid vessels via the bubble generating module, and is then driven the other half reciprocal cycle in a second direction along the flow path opposite to the first direction upwardly vertically through the other one of the spatially separated first and second fluid vessels back into the first one of the first and second fluid vessels via the bubble generating module; and repeating for a predetermined number of reciprocal half cycles said reciprocally driving fluid step so as to produce said medically useful bubbles of said medically desirable size, size distribution, concentration and homogeneity.

16. The invention of claim 15, wherein said predetermined number of reciprocal half cycles is a number selected from the group of numbers consisting of 0, even whole integers and odd whole integers.

* * * * *